United States Patent
Malcus-Vocanson et al.

(10) Patent No.: US 6,270,953 B1
(45) Date of Patent: Aug. 7, 2001

(54) METHOD FOR DETECTING AND/OR QUANTIFYING A GLIOTOXIC FACTOR

(75) Inventors: Carine Malcus-Vocanson, Brignais; Herve Perron, Lyons; Bernard Mandrand, Villeurbanne, all of (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/202,118

(22) PCT Filed: Sep. 12, 1997

(86) PCT No.: PCT/FR97/01620

§ 371 Date: Mar. 29, 1999

§ 102(e) Date: Mar. 29, 1999

(87) PCT Pub. No.: WO98/11439

PCT Pub. Date: Mar. 19, 1998

(30) Foreign Application Priority Data

Sep. 12, 1996 (FR) .................................................. 96 11347

(51) Int. Cl.⁷ ......................... C12Q 1/00; G01N 33/567; G01N 1/30
(52) U.S. Cl. .............................. 435/4; 435/7.21; 435/40.5
(58) Field of Search ................................. 435/47.21, 40.5

(56) References Cited

FOREIGN PATENT DOCUMENTS

| 0 667 354 A1 | 8/1995 | (EP) . |
| 0 731 179 A2 | 9/1996 | (EP) . |
| WO 95/21859 | 4/1995 | (WO) . |

OTHER PUBLICATIONS

Robert W. Keane, et al., "Rapid Communication; Activation of CPP32 During Apoptosis of Neurons and Astrocytes", *Journal of Neruoscience Research*, 48:168–180, 1997.

Rieger, Francois, et al. "Un factuer gliotoxique et la sclerose en plaques", Comptes Rendue de l'Academie des Sciences—Serie III, vol. 319, No. 4, Apr. 1996, Paris, pp. 343–350.

Giulian, Dana, et al., "Secretion of Neurotoxins by Mononuclear Phagocytes Infected with HIV–1", *Science,* vol. 250, Dec. 14, 1990, pp. 1593–1596.

Amouri, R., et al. "A New Gliotoxic Activity and its Implications for the Immunopathogenesis of Multiple Sclerosis", *Neuropsychiatrie,* vol. 9, No. 2, 1995, Munchen–Deisenhafen, p. 94.

Waring, Paul, et al. "Extracellular Calcium is not Required for Gliotoxin or Dexamethasone–Induced DNA Fragmentation: A Reappraisal of the Use of EGTA", International Journal of Immunopharmacology, vol. 17, No. 5, May 1995, Oxford, pp. 403–410.

Charles M. Poser, et al., "New Diagnostic Criteria for Multiple Sclerosis: Guidelines for Protocols," pp. 225–229, 1984.

E. Galiana, et al., Establishment of Permanent Astroglial Cell Lines, Able to Differentiate In Vitro, from Transgenic Mice Carrying the Polyoma Virus Large T Gene: An Alternative Approach to Brain Immortalization,: Journal of Neuroscience Research 26: pp. 269–277 (1990).

A. H. Wyllie, et al., "Chromatin Cleavage In Apoptosis: Association With Condensed Chromatin Morphology and Dependence on Macromolecular Synthesis," Journal of Pathology, vol. 142, pp. 67–77 (1984).

*Primary Examiner*—Christina Y. Chan
*Assistant Examiner*—Karen Clemens
(74) *Attorney, Agent, or Firm*—Oliff & Berridge, PLC

(57) ABSTRACT

The invention proposes a method for detecting and/or quantifying, in a biological sample, a cytotoxic factor, in particular a gliotoxic factor, with respect to adherent target cells, in particular macroglial cells, the toxicity of which causes the death by apoptosis of said cells. The method comprises providing an initial fraction of the sample, optionally enriched with the toxic factor by previous treatment, incubating the initial toxic factor with a reference culture medium comprising adherent target cells, and detecting and/or quantifying in the adherent target cells killed by apoptosis, by flow cytometry, at least one direct or indirect characteristic associated with the apoptotic adherent cells of the whole or part of the incubated medium, which, if it is present and/or is quantified, qualifies the sample as positive, i.e. as containing said toxic factor. The initial biological sample is preferably a urine specimen.

25 Claims, 2 Drawing Sheets

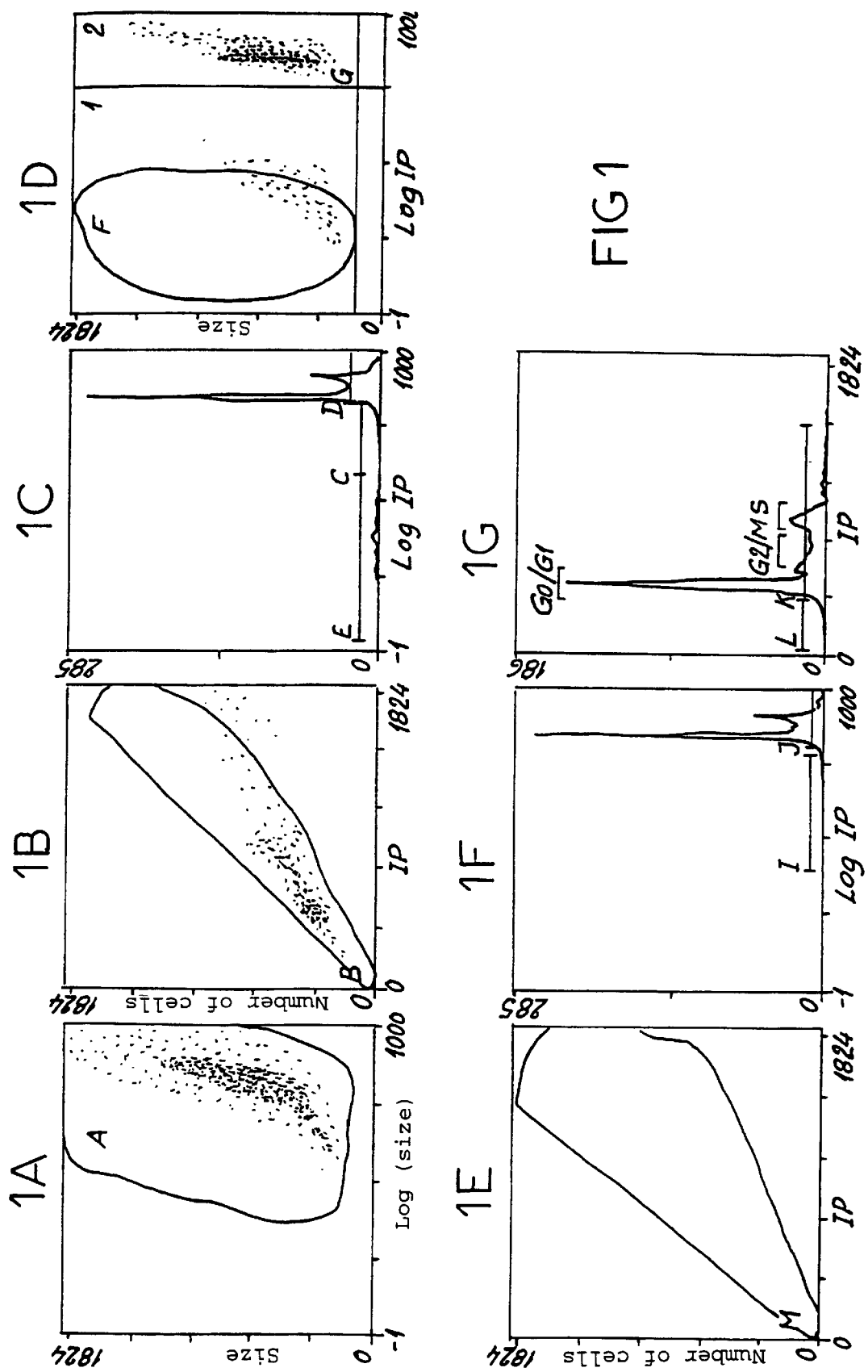

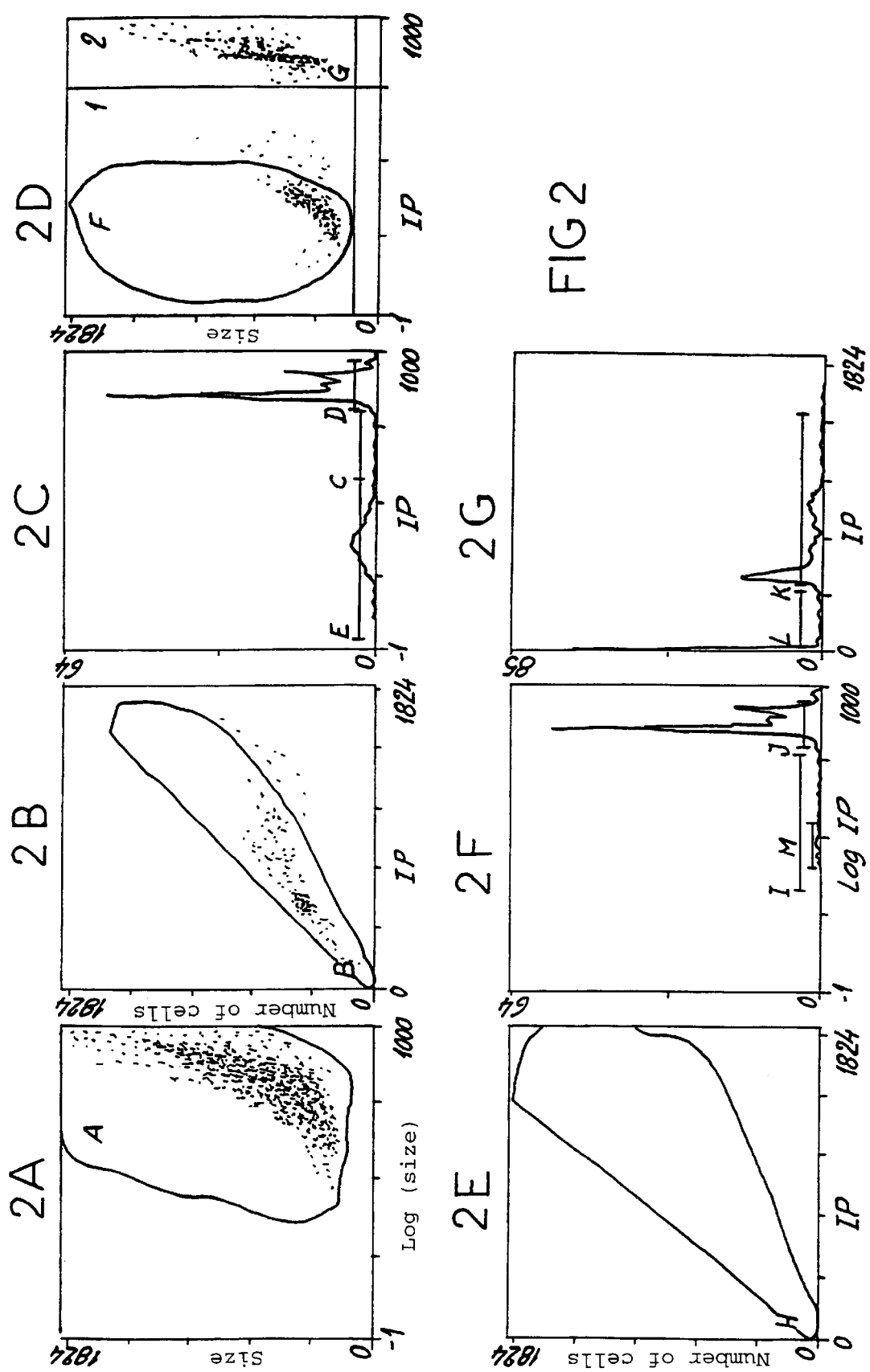

METHOD FOR DETECTING AND/OR QUANTIFYING A GLIOTOXIC FACTOR

This application is a national stage application of PCT/FR 97/01620, filed Sep. 12, 1997.

BACKGROUND OF THE INVENTION

1. Field of the Invention

The present invention relates to the determination, detection and quantification, in a biological sample, of a gliotoxic factor such as associated with multiple sclerosis.

2. State of the Art

A "biological sample" is understood, in particular, as being a specimen of the biological fluid type, live tissue or tissue fragment, mucus sample, organ or organ fragment type, or any culture supernatant obtained with the aid of an aforementioned specimen.

In accordance with document WO-A-95/21859, which is an application filed in the name of the applicant, a factor which is cytotoxic for glial cells (astrocytes, oligodendrocytes and microgliocytes), and which is termed gliotoxic factor below, has been isolated and/or characterized. While this factor is, in particular, associated with multiple sclerosis, it could also be associated with other neurodegenerative or autoimmune diseases.

In the absence of a complete sequence for this gliotoxic factor, the latter can be characterized either using a process (among others) which enables the factor to be isolated or purified or using different biological, biochemical or chemical properties or characteristics.

According to document WO-A-95/21859, this gliotoxic factor is characterized by all the following properties, considered separately or in combination:

it possesses a toxic activity for human or animal astrocytic cells, with its effect being that of eliciting cytomorphological disruption of their network of intermediate filaments and/or degradation of the proteins of these intermediate filaments and/or cell death, in particular by apoptosis, its activity is associated with at least one glycoprotein, this gliotoxic factor consists in the main, if not entirely, of a light-weight fraction which is centred on an apparent molecular weight of approximately 17 kD; this light-weight fraction is resistant, under standard non-denaturing conditions, to the hydrolytic action of pronase or trypsin or proteinase K; and this same light-weight fraction exhibits strong affinity for lectins, in particular concanavalin A.

Consequently, the detection and/or quantification of this gliotoxic factor in any biological sample is a worthwhile and effective analytical tool, in particular for the diagnosis of different pathologies, including multiple sclerosis, and the prediction, monitoring and therapy of this disease. Still in accordance with document WO-A-95/21859, the content and description of which are hereby incorporated into the present patent application by reference, a process for detecting and/or quantifying this gliotoxic factor in a biological sample, for example a sample of cerebrospinal fluid, has been described and proposed. Such a process comprises at least the following treatments:

a starting fraction of this sample, which is, where appropriate, enriched in the said gliotoxic factor by any appropriate prior treatment, is to hand, this starting fraction is incubated with a reference culture medium which, for example, comprises glial cells, in particular immortalized cells, for example astrocytic cells, and the dead or living glial cells are detected and/or quantified using any appropriate technique, for example using a calorimetric assay employing calcein AM and homodimeric ethidium, respectively.

Such a process, which is implemented for detecting and monitoring the therapy of multiple sclerosis, presupposes the existence of a so-called "invasive" specimen, for example of cerebrospinal fluid, that is to say which requires a prior medical or surgical act.

SUMMARY OF THE INVENTION

It has now been discovered that urine proves to be a particularly favourable biological fluid for detecting gliotoxic activity. This discovery was altogether surprising on account of the complex composition of urine and of its acidic nature and the presence of urea, which features were not, a priori, according to the general knowledge of the skilled person, compatible with detecting such a cellular activity.

It is therefore totally unexpected that, on the basis of this discovery, the inventors have developed a process for determining the gliotoxic factor in urine, which process additionally exhibits the advantage of using a non-invasive specimen, in the same way as any other sample obtained "invasively", for example a sample of cerebrospinal fluid, for detecting and/or quantifying the said factor in a patient.

Thus, the invention initially relates to a process for detecting and/or quantifying a gliotoxic factor in a biological sample, according to which process a starting fraction of the said sample, where appropriate enriched in the said gliotoxic factor by a prior treatment, is to hand, the said starting fraction is incubated with a reference culture medium comprising macroglial cells, for example immortalized macroglial cells, such as astrocytic cells, and the dead and/or living macroglial cells are detected and/or quantified, with the said biological sample being a urine sample.

A detection and/or quantification process which comprises a step of specifically detecting and/or quantifying the cells which have died by the apoptosis induced by the gliotoxic factor has then been defined.

According to document EP-A-0 731 179, a process is known for detecting preapoptotic lymphocytes by flow cytometry after the intracellular DNA of the said lymphocytes has been labeled. This document illustrates the use of flow cytometry for detecting cells which are in a preapoptotic state and which are non-adherent, that is to say in suspension.

The techniques for detecting apoptosis in adherent cells are not based on the same principle. As practised nowadays, and because of the fragility of apoptotic adherent cells, these techniques are based on visually observing apoptosis in situ by means of microscopy, with the apoptotic cells being counted. By way of example, mention may be made of the article by R. W. Keane, A. Srinivasan, L. M. Foster et al., J. Neurosci. Res., 1997, 48, 168–180, which deals with detecting adherent apoptotic cells of the nervous system.

It therefore proved necessary to have available a process which overcomes the abovementioned drawbacks of the techniques which are currently used for detecting apoptotic cells, that is a process which is, in particular, simple and relatively inexpensive and which, in addition, makes it possible to take into account the constraints associated with the fragility of apoptotic cells.

In addition, according to the invention, a process is supplied for detecting and/or quantifying, in a biological sample, a factor which is cytotoxic for target adherent cells and whose cytotoxicity induces the death of the said cells by apoptosis, according to which process a starting fraction of the said sample, where appropriate enriched in the said toxic factor by a prior treatment, is to hand, the said starting fraction is incubated with a reference culture medium comprising target adherent cells and at least one direct or indirect feature which is associated with the apoptotic adherent cells of all or part of the incubated medium, which feature, if it exists and/or is quantified, categorizes the said biological sample as being positive, that is to say containing the said toxic factor, is detected and/or quantified, by flow cytometry, the adherent cells which have died by apoptosis.

The above-defined process is advantageously applied to detecting the gliotoxic factor, and the target adherent cells are magroglial cells, in particular astrocytic cells.

Thus, according to at least one of the abovementioned features, the following is provided:
- a process which is able to comprise a "non-invasive" specimen,
- a process which is simple to implement, which is sensitive and which is specific for the gliotoxic factor.

It is known that apoptosis of macroglial cells is characterized, in particular, by:
- fragmentation of the cellular DNA of the apoptotic cells;
- preservation of the integrity of the cytoplasmic membrane of the apoptotic cells;
- alterations to the structure and size of the apoptotic cells.

Using the process of the invention, it is thus possible to determine:
- the ploidy of the macroglial cells, that is to say determine the quantity of DNA remaining in the cells after extraction of the DNA fragments, it being understood that the DNA quantity is preserved in non-apoptotic cells since there is no fragmentation; on the basis of the ploidy, it is also possible to study the cell cycle;
- the state of the macroglial cells; thus, cell morphology is determined by the size of the cells, for example using the so-called FALS (forward light angle scatter) technique, since the death of astrocytes by apoptosis brings about a decrease in their size; by the structure of the said cells, for example using the so-called Ss (side scatter) technique; and, where appropriate, by the presence and/or quantity of a protein, such as the glial fibrillar acid protein (GFAP), which makes it possible to discriminate between the cell subpopulations, for example using a labeled anti-GFAP antibody which can be identified directly or indirectly.

For the purpose of specifically detecting and/or quantifying, by flow cytometry, macroglial cells which have died by apoptosis, the said process of the invention comprises at least one of the following protocols (1) to (3); advantageously, protocols (1) and (2) or (1) and (3) are employed in combination.

Protocol (1)
- detaching the adherent macroglial cells,
- treating the cells which have thus been detached with an agent for cell fixation and permeabilizing the cytoplasmic membrane of the said cells,
- extracting intracellular DNA fragments resulting from the apoptosis,
- labeling the remaining cellular DNA with an appropriate label, and
- detecting, by flow cytometry, the ploidy of the macroglial cells.

Advantageously, the agent for cell fixation and permeabilization of the cytoplasmic membrane of the cells is ethanol and the label for the DNA is propidium iodide (PI).

Protocol (2)
- inducing a necrosis, in particular by incubation, in a sample of living macroglial cells which is different from the sample to be analyzed,
- labeling the DNA debris which result from the necrosis, with the said debris being associated with fragments of the cytoplasmic membrane of the necrotic macroglial cells, and with the labeling being effected after detaching the said cells,
- locating, in flow cytometry, the cells which have died by necrosis and appropriately adjusting the cytometer, thereby enabling the cells which have died by necrosis to be excluded during the step of detecting the cells which have died by apoptosis,
- detecting the cells which have died by apoptosis.

Protocol (3)
- dividing the cells of the biological sample into two equal parts and detaching the cells,
- detecting, by flow cytometry, in one of the two parts, the macroglial cells which have died by apoptosis or by necrosis, on the one hand, and/or the living macroglial cells, on the other hand, in which step the said fraction is treated with an agent for cell fixation and for permeabilization of the cytoplasmic membrane; the DNA fragments are extracted; the intracellular DNA is labeled with a label and the remaining intracellular DNA is detected,
- detecting, by flow cytometry after fixation without extraction, in the other of the two parts, the living macroglial cells and the apoptotic macroglial cells, on the one hand, and/or the necrotic macroglial cells, on the other hand,
- deducing, from the detections effected on each of the two parts, the quantity of apoptotic macroglial cells.

Using protocol (2) or (3) as defined above, it is possible to distinguish the apoptotic cells from necrotic cells. It is known that the phenomena of necrosis result in rupture of the cell wall and release of the cell constituents. Necrotic cells therefore differ from other cells, i.e. living or apoptotic cells, in that the integrity of their cytoplasmic membrane is not preserved. This can be demonstrated either on the basis of an isolated experiment carried out after inducing necrosis in living macroglial cells in order to locate the necrotic cells obtained and to adjust the cytometer appropriately so as to be able to exclude these necrotic cells in the final determination of the apoptotic cells (protocol 2); or by a parallel study carried out on two identical subpopulations derived from the same macroglial cells after potentially inducing apoptosis in these cells, with the said cells being treated in two different ways: namely, on the one hand, after fixing with ethanol and extracting the DNA fragments, the labeling with IP enables the living cells to be distinguished from the dead cells (necrosis and apoptosis); on the other hand, after fixing without extracting the DNA fragments, the labeling with IP thus makes it possible to distinguish the necrotic cells from the living or apoptotic cells (since, in the absence of extraction, the DNA fragments are retained in the interior of the apoptotic cells); and then it is possible to determine, by deduction, the proportion of each subcategory of cells and hence the proportion of apoptotic cells (protocol 3).

This distinction between necrotic cells and apoptotic cells is necessary, in particular, when interfering medicines are given to patients, with the said substances being able to induce phenomena involving overlapping of the necrotic cell population and the apoptotic cell population, which phenomena result, in particular, in the generation of falsely positive results in tests for detecting apoptosis. Thus, this interference has been observed when using biological samples, for example urine samples, derived from patients who have undergone a treatment with interfering medicinal substances, for example methotrexate or dextropropoxyphene.

The application of the process of the invention for specifically detecting and/or quantifying apoptotic macroglial cells to a urine sample makes it possible to obtain a particularly simple bioassay which is sensitive and specific for the gliotoxic factor, for example with regard to assisting in the diagnosis of multiple sclerosis, which diagnosis currently requires a large number of different tests or examinations over a period of time which can be relatively long.

According to one particular embodiment of the process of the invention, this can comprise, before the step of detecting and/or quantifying the apoptotic macroglial cells, a step of detecting cell viability. To this end, the starting fraction is inoculated into the reference culture medium and the rate of proliferation of the macroglial cells is compared with a reference value, below which the said fraction, which is said to be positive, is retained for then being subjected to the step of specifically detecting the apoptosis of the microglial cells, in order to categorize or not categorize the biological sample as being truly positive.

During this step of detecting cell viability, the rate of proliferation of the macroglial cells can be obtained by staining the mitochondria of the macroglial cells of the culture medium, for example with methyltetrazolium bromide, and then measuring the optical density of the stained culture medium. The calorimetric assay of living cells with methyltetrazolium (MTT), as described in document WO-A-95/21859, may be mentioned by way of example.

During the step of specifically detecting the apoptosis of the macroglial cells, it is advantageously possible to additionally determine the presence and/or quantity of a protein, such as the glial fibrillary acidic protein (GFAP), which makes it possible to discriminate between subpopulations of cells, for example using an anti-GFAP antibody which can be identified directly or indirectly.

Determination of the changes which take place within the phospholipids of the cytoplasmic membrane of the apoptotic cells, without affecting its integrity, and evidence for which is provided by annexin V, can also be envisaged for complementing the process of the invention.

The starting fraction of the biological sample in which the gliotoxic factor is detected and/or quantified can be obtained by enriching or purifying the biological sample in gliotoxic factor. This enrichment or purification is, in particular, achieved using at least one of the following treatments, namely precipitation of the protein fraction, for example with ammonium sulfate, exclusion and/or ion exchange chromatography, one-dimensional or two-dimensional electrophoresis, or bringing into contact with protein A or a lectin, for example concanavalin A.

The reference culture medium in which the said starting fraction is incubated preferably comprises an immortalized cell line of macroglial cells, for example an immortalized astrocyte cell line.

The macroglial cells under consideration in accordance with the present invention comprise, in particular, astrocytes and oligodendrocytes.

BRIEF DESCRIPTION OF THE DRAWINGS

The present invention is now described by reference to the following examples 1 to 7 and to the drawings in which:

FIG. 1 (A to G) depicts the histograms which are obtained by flow cytometry for a sample which contains only a few necrotic cells and does not contain any apoptotic cells, FIG. 2 (A to G) depicts the histograms which are obtained by flow cytometry for a sample which contains apoptotic cells.

The letters A to L which appear in the histograms correspond to the location of cells visualized in flow cytometry.

DETAILED DESCRIPTION OF PREFERRED EMBODIMENTS

EXAMPLE 1

Step of detecting apoptosis by flow cytometry.

The immortalized astrocyte cell line is obtained in accordance with the paper by E. Galiana, I. Borde, P. Marin, M. Rassoulzadegan, F. Chuzin, F. Gros, P. Rouget and C. Evrard, Establishement of permanent astroglial cell lines, able to differentiate in vitro, from transgenic mice carrying the polyoma virus large-T gene: an alternative approach to brain cell immortalization, Journal of Neuroscience Research, 1990; 26; 269–277, the content of which paper is hereby incorporated into the present description by reference.

The medium termed medium M is made up as follows: DMEM (400 µl/200 ml)/F12 (1/1)+10% un-decomplemented FCS+penicillin/streptomycin (antibiotic)+fungizone (antifungal agent) (20 µl/40 ml).

The cytometer employed is a Coulter Epics XL cytometer (from Coultronics, France). The adjustment of the program employed is as follows:

| flow rate: 60 µl/min liquid matrix: IsoFlow (commercial name) fluorescence: | | |
|---|---|---|
| | Voltage (V) | Gain |
| FL1 (FITC) | 605 | 1 |
| FL3 (IP) | 715 | 2 |
| AUX (FL3) | 190 | 1 |
| FS | 423 | 1 |
| SS | 800 | 1 |

FL: fluorescence; FITC: fluorescein isothiocyanate; IP: propidium iodide; AUX: auxiliary channel permitting double adjustment on propidium iodide; FS: diffraction; SS: refraction at 90°.

Experimental Protocol:

24- or 48-well plates coated with 12.5 µg/ml poly-L-lysine are prepared in advance:

The following manipulations are carried out in a sterile atmosphere (laminar flow):

tubes containing 4 ml of poly-L-lysine (frozen at −20° C.) are diluted 1/10 in distilled $H_2O$, 250 µl of this solution are added/well, the plates are left to incubate for 2 hours at least, the solution is aspirated, the plates are rinsed with 500 µl of distilled $H_2O$/well (24-well plates) or 250 µl/well (48-well plates), the distilled $H_2O$ is aspirated, the uncovered plates are left to dry in the flow (for from a few minutes to 30 min), the plates are covered and stored in the flow.

First day:

The cells contained in a 250 $cm^2$ plate are trypsinized (solution prepared from a 1/250 solution of trypsin (S1: 45 ml) and a 1% solution of EDTA (S2: 5 ml) and stored at +4° C.):

The plate is taken from the incubator. The medium which covers the cells is aspirated (10 ml pipette) and discarded. The adherent cells are rinsed with from 10 to 15 ml of DMEM/F12 (1/1), which volume is then aspirated. From 1 to 1.2 ml of trypsin/EDTA are added and the cells are put back into the incubator for 10 min. They are mechanically detached from their support using a pipette containing 10 ml of medium M. After homogenization, they are washed in a further 20 ml of DMEM/F12 and then centrifuged for 10 min at 1500 rpm (18° C.).

The supernatant is carefully removed. The cells are taken up in 2 ml of DMEM/F12 and homogenized at length. They are once again washed in 25 ml of DMEM/F12 and then centrifuged (10 min, 1500 rpm, 18° C.). The supernatant is discarded. The cells are taken up in 2 ml of medium and homogenized at length in order to obtain a suspension which is as uniform as possible. From 1 to 5 ml of medium are added depending on the size of the pellet.

The cells are counted directly in a Tomas cell. The cell concentration is adjusted to 10,000 cells/ml, by diluting in M medium, in order to deposit 20,000 cells/well, that is 2 ml/well in the case of a 6-well plate. For example, for eight 6-well plates, 8×6×2 ml of suspension, that is 96 ml, are required; 120 ml (3×40 ml) of suspension are prepared; approximately 25 ml of suspension is therefore left over, which volume will be used for putting the remaining cells back into culture, by adding them to this remaining 25 ml volume.

The plates which have thus been prepared are covered with a protective film in order to avoid evaporation.

Second day:

The gliotoxic factor is added to each well at the rate of from 60 to 80 $\mu$l/well in accordance with the presumed quantity of toxic factor in the sample (10 $\mu$l/well in the case of urine samples, and from 10 to 50 $\mu$l/well in the case of purified fractions and other samples).

The plate is taken from the incubator. The protective film is removed. The factor is added in triplicate in two or three successive wells. A new protective film is put in place. The plates are put back in the incubator (37° C., 5% $CO_2$ 95% $H_2O$) for 72 hours.

Fifth day:

The state of the living cells which are present in the wells is assessed by flow cytometry after labeling with propidium iodide in order to detect the apoptotic cells.

The plates are taken out of the incubator. The protective film is taken off. The medium is aspirated (straight, unplugged Pasteur pipettes) taking care not to aspirate the adherent cells at the bottom of the wells. The cells are rinsed with 2 ml of PBS.

The cells are then detached gently (non-enzymically) by incubating with a PBS EDTA solution (from 1 to 2 ml/well) (37° C., 5% $CO_2$ 95% $H_2O$ for 10 min) and then dissociated mechanically. Such a treatment safeguards the adherent cells, in particular the apoptotic cells. The wells are rinsed with PBS in order to recover the last cells at the bottom of these wells. Two PBS washes are carried out.

The cells are fixed with 70% ethanol, which treatment leads to the formation of pores in the cell membrane and induces its permeabilization. 2 ml of 70% ethanol (deep-frozen) are added to each well for this purpose. The cells are fixed at −20° C. for 1 hour. After the plates have been centrifuged in order to remove the alcohol, they are washed with PBS.

The cells, which have thus been permeabilized, are treated in order to extract the DNA fragments generated by the apoptosis. The extraction buffer is prepared for immediate use:

9 ml of 0.05 M $Na_2HPO_4$ 1 ml of 25 mM citric acid 0.1% triton X-100.

The cell pellet obtained in the following step is taken up in 2 ml of this buffer and incubated at +4° C. for 1 hour.

After a centrifugation to remove the buffer, the pellet is washed with PBS.

Where appropriate, a labeling with anti-GFAP antibody can be carried out in order to visualize the cells and their astrocytic features. In this case, the cell pellet is taken up in 50 $\mu$l of 5% BSA+50 $\mu$l of 1% saponin in PBS+20 $\mu$l of anti-GFAP antibody (prepared in rabbits) diluted 1/100 and then incubated at ambient temperature for 30 min in the dark. After having been washed twice in PBS, the cells are counterlabeled (addition of 50 $\mu$l of 5% BSA+50 $\mu$l of 1% saponin in PBS+20 $\mu$l of fluorescein (FITC)-labeled anti-rabbit IgG antibody diluted 1/10), followed by incubation at ambient temperature for 15 min in the dark. The cells are washed twice with PBS.

After the possible labeling with GFAP, the suspensions can be stored for from 1 to 2 days in PBS.

A labeling with propidium iodide (PI), which is a label for DNA, is carried out by adding 100 $\mu$l of RNase (that is 50 IU) and 250 $\mu$l of 50 $\mu$g/ml PI (in this order) to the cell pellet.

The results are read in a cytometer within 15 min.

The labeling with PI, where appropriate combined with a GFAP labeling, is used to identify and locate the astrocytes. The analysis of each sample is carried out on 3000 cells (cf. FIGS. 1A, 1B and 1C, and 2A, 2B and 2C).

When this method is used, the PI-labeled nuclei of the living cells are visualized in the form of 3 peaks of fluorescence which represent, respectively, the G0/G1, S and G2/M phases of the cell cycle, as shown in FIG. 1G. By contrast, the PI-labeled nuclei of the apoptotic cells, whose fragmented DNA has been previously extracted, are visualized in the form of a relatively diffuse single peak which is located in the sub-G1 region, as is shown in FIG. 2G. In order to demonstrate that the subdiploid (sub-G1) peak is solely due to the apoptotic cells, and in order to eliminate interfering elements (necrotic cells and debris), the cells are first of all analyzed under experimental conditions which make it possible to induce death by necrosis (Wyllie et al., J. Pathol., 1984, 142, 67–77) (cf. FIGS 1D and 1E, and 2D and 2E). This makes it possible to adjust the settings of the cytometer so as to eliminate non-apoptotic cells. The apoptotic cells are then analyzed as previously described (cf. FIGS. 1F and 2F, in which the cells which have died by apoptosis can be seen).

The results which were obtained are compiled in Table I, which is presented at the end of the description.

EXAMPLE 2

Step of determining cytotoxicity in the immortalized astrocyte cell line, constituting, in particular, the step of detecting cell viability.

As pointed out in the description, it is advantageously possible to carry out a step of detecting cell viability before the flow cytometry detection step. The experimental protocol described in Example 1 is repeated up to the fifth day.

Fifth day:

The quantity of living cells remaining in the wells is evaluated by incorporating MTT (tetrazolium bromide) and then lyzing with acidic isopropanol in order to detect the formazan crystals which are obtained after incorporating MTT into the living cells.

An 0.5 mg/ml solution of MTT in DMEM/F12 is prepared by diluting the MTT (deep-frozen) 1/10 in the DMEM/F12.

The plates are taken out of the incubator. The protective film is taken off. The medium is aspirated taking care not to aspirate the adherent cells at the bottom of the wells. 250 µl of the MTT solution (in DMEM/F12) are added/well. The plates are left to incubate for at least 3 hours in the incubator (37° C.).

The acidic isopropanol (addition of 40 µl of 1N HCl to each 1 ml of pure isopropanol) is prepared while ensuring that there is sufficient for 100 µl/well in the case of the 48-well plates.

As an example, 48×4×100, that is approximately 20 ml, of acidic isopropanol are required for four 48-well plates. 30 ml of isopropanol+1.2 ml of 1N HCl are prepared.

The plates are taken out of the incubator and the MTT solution is aspirated; 100 µl of acidic isopropanol are then added per well.

If the color is too dark, a further 50 µl of acidic isopropanol are added per well.

The resulting solution in each well is then transferred to a 96-well plate so that it can be read on a microplate reader. 70 µl are recovered from each well of a 48-well plate for transfer to a 96-well plate.

The ODs are read at 570 nm (ref. 630 nm).

The values which are obtained are interpreted with suitable software in order to obtain a percentage glyotoxicity value:

The mean and standard deviation of the OD values obtained for all the wells which contain cells which have grown normally (100% viability) are calculated in the case of each plate; the cutoff is obtained by difference:

cutoff=mean−2× standard deviation (=CO).

Each tested sample is represented by 3 OD values (corresponding to the 3 wells to which 10 or 20 µl of sample were added); the mean of the 3 OD values (=ODc) is calculated; thus, an OD difference (OD) and a percentage toxicity (% tox) are obtained for each sample:

OD=CO−ODc

% tox=(1−(ODc/CO))×100.

If the 3 wells for a particular sample give 3 different OD values, the sample is retested.

EXAMPLE 3

Techniques for enriching the biological sample in gliotoxic factor, for the purpose of obtaining a fraction which is subjected to the step described in Example 1, and, where appropriate, the determination step described in Example 2

3.1) Precipitation of the protein fraction

A 60% by weight solution of ammonium sulfate in water is employed.

3.2) Exclusion chromatography

A TSK G 2000 column (marketed by Supelco), in high-pressure liquid phase, is used with a pH 6.8 buffer and with 0.1 M phosphate and 0.1 M sodium sulfate.

The acquisition time is 60 minutes and the volume of the injected sample is 1 ml.

3.3) Ion exchange chromatography

A fast-flow DEAE-Sepharose (DEAE: diethylaminoethyl) column (marketed by Pharmacia) is used, in high-pressure liquid phase, with a 20 mM tris buffer, pH 7.5, and with elution being carried out in steps using an NaCl solution of from 100 mM to 1 M, with the useful fraction being at 200 mM.

3.4) One-dimensional or two-dimensional electrophoresis

The SDS PAGE (polyacrylamide gel electrophoresis) technique is employed using a 17% acrylamide gel. The electrogram is transferred onto a Porablot (commercial name) membrane and staining is carried out using an amido black stain.

EXAMPLE 4

Biological equivalence, for determining the gliotoxic factor, of the urine and cerebrospinal fluid from a patient suffering from multiple sclerosis.

4.1) Samples of cerebrospinal fluid, on the one hand, and of urine, on the other hand, from patients suffering from multiple sclerosis (MS) are subjected, in equal volume, to the same pretreatment involving the separation of the protein fraction, as described in Example 3.1; this protein fraction is then subjected to exclusion chromatography as described in Example 3.2 and to ion exchange chromatography as described in Example 3.3.

In both types of chromatography, the urine and the cerebrospinal fluid are resolved in the same manner and exhibit a fraction which is situated between 15 kD and 20 kD in the case of the exclusion chromatography and eluted by 200 mM NaCl in the case of the ion exchange chromatography.

This fraction is tested using the step described in Example 2 and displays gliotoxic activity.

4.2) Samples of cerebrospinal fluid, on the one hand, and urine, on the other hand, from MS patients are subjected to one-dimensional electrophoresis as described in Example 3.4. A cutoff threshold situated between 15 and 25 kD, corresponding to a cytotoxic activity, is observed in both cases.

4.3) Samples of urine from MS patients, and from healthy patients and patients suffering from other neurological diseases, are subjected to the step described in Example 2.

The results, which are compiled in Table II (which appears at the end of the description) demonstrates that urine is relatively specific as a biological sample for determining the gliotoxic factor.

EXAMPLE 5

Use of urine samples to determine, by detecting cytotoxicity, the gliotoxic factor in a substantial population.

The urine samples are tested using the protocol identified in Example 2.

The patients suffering from multiple sclerosis are patients who are either hospitalized in a neurology department (~90% for a corticoid flash at the time of an episode) or in a specialized reeducation department (patients who are in general not suffering from episodes and of whom ~50% are in the chronic stage of the disease). The patients suffering from other diseases are patients who are hospitalized in a neurology department (without restriction as regards pathology, age or sex). The results obtained on 108 urine samples from patients suffering from multiple sclerosis (categorized according to Poser's criteria as being certain or probable, C. M. Poser et al., New diagnostic criteria for multiple sclerosis: guidelines for research protocols, in "The Diagnosis of Multiple Sclerosis", C. M. Poser, D. W. Paty, L. Scheinberg, W. I. Mac Donald, G. C. Ebers, pp. 225–229, 1984, Thieme Stratton Inc., New York), 116 urine samples from patients suffering from other neurological diseases and 29 urine samples from healthy control subjects are presented in Table III (which appears at the end of the description).

The results obtained demonstrate that the test is positive in the case of 98 patients suffering from multiple sclerosis and negative in the case of 10 patients suffering from multiple sclerosis. However, this test generates 40 false positives in patients suffering from other neurological diseases and 2 false positives in the healthy control subjects.

The test defined in Example 2 is not therefore entirely specific on its own.

EXAMPLE 6

Use of cytometry to determine the state of the cells

The method described in Example 1 makes it possible, at one and the same time, to judge the state of the astrocytes and also detect cell death (in particular differentiation between necrosis and apoptosis) and the ploidy.

This method is based on using flow cytometry (FC) for detecting i) cell morphology (FALS (forward light angle scatter) makes it possible to visualize the size of the cells and SS (side scatter) makes it possible to visualize their structure), ii) the astrocytic features (labeling with anti-GFAP (glial fibrillary acidic protein) antibody, visualisation with FITC-labeled anti-Ig antibody), iii) the ploidy (labeling with propidium iodide (PI) after fixing with 70% ethanol and extracting the possible DNA fragments) and consequently the cell cycle. This latter step (using PI) makes it possible to differentiate the cell debris, the necrotic cells, the apoptotic cells and the diploid cells which are capable of dividing normally.

30 false positives obtained in Example 5 were then tested and it was observed that while the non-MS urine samples produced necrosis and/or proliferation inhibition effects, but no apoptotic phenomena, the MS urine samples at least gave rise to apoptosis.

EXAMPLE 7

Combination of the methods described in Examples 1 and 2.

The combination of the two tests was then evaluated on 30 multiple sclerosis urine samples and 30 neutrological control (non-MS) urine samples, after the step of detecting cell viability. The results of the study are given in Table IV, which appears at the end of the description. As can be seen, the results obtained demonstrate a high degree of sensitivity and a high degree of specificity.

TABLE I

Results obtained by the process of the invention as described in Example 1, i.e. by flow cytometry after extracting the DNA fragments and staining the DNA with propidium iodide

|  | Definite MS cases | Cases of other neurological diseases | Healthy control subjects |
| --- | --- | --- | --- |
| Number of patients tested | 35 | 36 | 15 |
| Apoptosis | 32 i.e. 91% | 5 i.e. 14% | 0 i.e. 0% |
| Absence of apoptosis | 3 i.e. 9% | 31 i.e. 89% | 15 i.e. 100% |

TABLE II

Astrocyte culture gliotoxicity test using urine samples (cf. Example 4)

| MTT test | MS (n = 30) | OND* (n = 32) | Healthy control subjects (n = 19) |
| --- | --- | --- | --- |
| Positive | n = 28 | n = 5 | n = 1 |
| Negative | n = 2 | n = 27 | n = 18 |

OND: other, non-MS, neurological diseases

TABLE III

Astrocyte culture gliotoxicity test using urine samples (cf. Example 5)

| MTT test | MS (n = 108) | OND* (n = 116) | Healthy control subjects (n =29) |
| --- | --- | --- | --- |
| Positive | n = 98 91% | n = 40 34% | n = 2 7% |
| Negative | n = 10 9% | n = 76 66% | n = 27 93% |

OND: other, non-MS, neurological diseases

TABLE IV

Astrocyte culture gliotoxicity test using urine samples (cf. Example 7)

| Test using FC** | MS (n = 30) | OND* (n = 30) |
| --- | --- | --- |
| Necrosis or inhibition of proliferation | n = 1 3% | n = 30 100% |
| Apoptosis | n = 29 97% | n = 0 0% |

OND: other, non-MS1 neurological diseases
FC: flow cytometry

What is claimed is:

1. A process for detecting, in a urine sample, a factor that is cytotoxic for target adherent macroglial cells and whose cytotoxicity induces death of said cells by apoptosis, said process comprising:

incubating said sample with a reference culture medium comprising said target macroalial adherent cells; and detecting and/or quantifying the target adherent macroglial cells that have died by apoptosis using flow cytometry, thereby indicating the presence of a cytotoxic factor in the biological sample.

2. A process according to claim 1, wherein the target adherent macroglial cells are astrocytic cells.

3. A process according to claim 1, wherein said process of detecting and/or quantifying the target adherent macroglial cells that have died by apoptosis comprises:

detaching the adherent macroglial cells, treating the cells that have thus been detached with an agent for cell fixation and permeabilization of the cytoplasmic membrane of said cells, extracting intracellular DNA fragments resulting from apoptosis, labeling the remaining cellular DNA with an appropriate label, adjusting the flow cytometer to exclude the cells which have died by necrosis, and detecting, by flow cytometry, the ploidy of the macroglial cells, thereby detecting the cells that have died by apoptosis.

4. A process according to claim 3, wherein the agent for cell fixation and permeabilization of the cytoplasmic membrane of the cells is ethanol.

5. A process according to claim 3, wherein the label for the DNA is propidium iodide (PI).

6. A process according to claim 3 in which the cells which have died by necrosis are determined by:

inducing necrosis in a second sample of living macroglial cells, detaching the cells, labeling the DNA debris resulting from necrosis, said debris being associated with fragments of the cytoplasmic membrane of the necrotic macroglial cells, and detecting and/or quantitating the cells that have died by necrosis.

7. A process according to claim 1, wherein said process of detecting and/or quantifying the target macroglial cells that have died by apoptosis using flow cytometry comprises:

dividing the cells in the reference culture medium containing the incubated sample into two equal parts and detaching the cells, and in one part, the cells are treated with an agent for cell fixation and for permeabilization of the cytoplasmic membrane, the DNA fragments are extracted the remaining intracellular DNA is labeled and detected by flow cytometry, thereby distinguishing the living cells from the cells that have died by necrosis or apoptosis, in the second part, the cells are treated with an agent for cell fixation and the remaining intracellular DNA is labeled and detected by flow cytometry, thereby distinguishing the living cells and the cells that have died by apoptosis from the cells that have died by necrosis, and deducing, from the detection and/or quantification of part one and part two, the quantity of apoptotic macroglial cells.

8. A process according to claim 1, wherein the reference culture medium comprises an immortalized cell line of cells.

9. A process according to claim 8, wherein said immortalized cell line is an astrocyte cell line.

10. A process according to claim 1, wherein, prior to detecting and/or quantifying the target macroglial cells that have died by apoptosis, the cell viability is detected, said process comprising:

comparing the rate of macroglial cell proliferation in the reference culture medium with a value obtained from untreated macroglial cells in culture medium.

11. A process according to claim 10, wherein during the step of detecting cell viability, the rate of proliferation of the macroglial cells is obtained by staining the mitochondria of the macroglial cells in the culture medium and then measuring the optical density of the cells in the culture medium.

12. A process according to claim 11, wherein the mitochondria is stained with methyltetrazolium bromide.

13. A process according to claim 1, wherein, during the step of detecting and/or quantifying the target macroglial cells that have died by apoptosis, the presence and/or quantity of a protein is determained to discriminate between subpopulations of cells.

14. A process according to claim 13, wherein said protein is a glial fibrillary acidic protein (GFAP).

15. A process according to claim 14, wherein the presence and/or quantity of said GFAP protein is determined using an anti-GFAP antibody.

16. A process according to claim 1, wherein, prior to incubating the sample with a reference culture medium, said sample has been enriched in said cytotoxic factor.

17. A process according to claim 16, wherein the cytotoxic factor in the urine sample enriched or purified using at least one treatment selected from the group consisting of precipitation of the protein fraction, exclusion and/or ion exchange chromatography, one-dimensional or two-dimensional electrophoresis, two bringing the sample into contact with protein A or a lectin.

18. A process for detecting, in a biological sample, a factor that is gliotoxic for target macroglial cells, wherein the biological sample is a urine sample, said process comprising:

incubating said sample with a reference culture medium comprising said target macroglial cells; and detecting and/or quantifying the target macroglial cells that have died by apoptosis, thereby detecting the presence of a gliotoxic factor in the biological sample.

19. A process according to claim 18, wherein, prior to detecting and/or quantifying the target macroglial cells that have died by apoptosis, the cell viability is detected, said process comprising:

comparing the rate of macroglial cell proliferation in the reference culture medium with a value obtained from untreated macroglial cells in culture medium.

20. A process according to claim 19, wherein during the step of detecting cell viability, the rate of proliferation of the macroglial cells is obtained by staining the mitochondria the macroglial cells in the culture medium and then measuring the optical density of the cells in the culture medium.

21. A process according to claim 18, wherein said gliotoxic factor is associated with multiple sclerosis.

22. A process according to claim 18, wherein, prior to incubating the sample with a reference culture medium, said sample has been enriched in said gliotoxic factor.

23. A process according to claim 22, wherein the gliotoxic factor in the urine sample is enriched or purified using at least one treatment selected from the group consisting of precipitation of the protein fraction, exclusion and/or ion exchange chromatography, one-dimensional or two-dimensional electrophoresis, and bringing the sample into contact with protein A or a lectin.

24. A process according to claim 23, wherein the protein fraction is precipitated with ammonium sulfate.

25. A process according to claim 23, wherein said protein A or lectin is concanavalin A.

* * * * *